United States Patent [19]

Koshiishi et al.

[11] 4,182,668
[45] Jan. 8, 1980

[54] ION SELECTIVE ELECTRODE

[75] Inventors: Kiyozo Koshiishi, Sagamihara; Takashi Mizusaki, Hachioji, both of Japan

[73] Assignee: Olympus Optical Co., Ltd., Tokyo, Japan

[21] Appl. No.: 950,295

[22] Filed: Oct. 11, 1978

[30] Foreign Application Priority Data

Oct. 20, 1977 [JP] Japan .......................... 52/140936[U]

[51] Int. Cl.² ........................................... G01N 27/30
[52] U.S. Cl. ................................................ 204/195 L
[58] Field of Search ........... 204/195 L, 195 M, 195 P; 324/29

[56] References Cited

U.S. PATENT DOCUMENTS

| | | | |
|---|---|---|---|
| 3,483,112 | 12/1969 | Ross | 204/195 L |
| 3,598,713 | 8/1971 | Baum et al. | 204/195 L |
| 3,647,666 | 3/1972 | Simon et al. | 204/195 |
| 3,840,452 | 10/1974 | Baum et al. | 204/195 M |

Primary Examiner—G. L. Kaplan
Attorney, Agent, or Firm—Haseltine, Lake & Waters

[57] ABSTRACT

An electrode sensitive to ions in solution comprises an outer tubular body having an opening at its one end, an inner tubular body secured to the other end of the outer tubular body and having an opening at its one end, a tip member threadingly engaged to one end of the outer tubular body and having an aperture at its one end, a first porous membrane provided between the tip member and one end of the outer tubular body to define a first reservoir together with the outer tubular body, a sealing member provided around the periphery of the first porous membrane, a second porous membrane provided at one end of the inner tubular body to define a second reservoir therein, an ion-exchanger liquid accommodated in the first reservoir and in contact with the first porous membrane directly, an internal reference solution accommodated in the second reservoir, and an inner reference electrode connected to a shielded cable extended through the other end of the outer tubular body and dipped in the internal reference solution.

The tip member for holding the first porous membrane is formed by a metal tube and at least a portion of the metal tube in contact with a solution to be tested is coated with an insulating film.

5 Claims, 3 Drawing Figures

ION SELECTIVE ELECTRODE

BACKGROUND OF THE INVENTION

The present invention relates to an ion selective electrode and more particularly to an improvement of a tip member for use in an ion selective electrode of a liquid-membrane type in which the tip supports a porous membrane impregnated with an ion-exchanger liquid for exchanging a specific ion at an interface between two immiscible phases, i.e., the ion-exchanger liquid and a solution to be tested.

Such ion selective electrode is shown in FIG. 1 and comprises an outer tubular body 1 and an inner tubular body 2 which are formed integrally with each other. The end portion of the outer tubular body 1 is threadingly engaged with an annular tip 3 and a porous membrane 4 is clamped and held between the lower end of the inner tubular body 2 and the tip 3 to define two reservoirs which are adjacent to the membrane 4. The outer reservoir contains an ion-exchanger liquid 5 for sensing a specific ion therein and the inner reservoir contains an internal reference solution 6 therein. In the inner reservoir there is also provided with an inner electrode 8 of AgCl or the like which is connected to a shielding wire 7 led in from the other end portion of the outer tubular body 1 and which is immersed in the internal reference solution 6. The outer end of the outer tubular body 1 is threadingly engaged with a cap 9.

In the ion selective electrode shown in FIG. 1 the porous membrane 4 holds the ion-exchanger liquid 5 and the internal reference solution 6 and defines an interface between a solution to be tested (not shown) and the liquids 5 and 6. The porous membrane 4 is also formed by a porous material which has a limited size of meshes thereof, such as plastic film, ceramic or the like. The porous membrane 4 is further held tightly by the inner tubular body 2 and the tip 3 in order to prevent any small current leakage. The porous membrane 4 is further more formed by a hydrophobic material or subjected to hydrophobic coating treatment so that the porous membrane 4 is effectively impregnated with the organic ion-exchanger liquid 5 and is not impregnated with the internal reference solution 6. The solution to be tested forms substantially together with the ion-exchanger liquid 5 an interface therebetween so that the electric resistance between the inner electrode 8 and a reference electrode (not shown) depends on the area and the thickness of the porous membrane 4 and becomes very high such as $10^9$ Ω·cm or more. Therefore, it is preferable to use plastic material having high insulation resistance as the outer tubular body 1 and the tip 3 which are in contact with the test solution.

Such an electrode forms a clearance between the plastic tip 3 and the porous membrane 4 by the temperature changes of the test solution and the measuring atmosphere and the swell of the electrode by moisture absorption, so that the current leakage becomes large resulting in worse of performance and it is liable to enter air bubbles in the clearance resulting in inferior durability. In case of designing an electrode for effecting stable operation over a long period of time against the temperature change and the swell by moisture absorption by tightly holding the porous membrane to the same electrode as that shown in FIG. 1, the outer diameter of the electrode must be made large and thus it is necessary to increase the length d of the aperture 10 of the tip 3 which performs ion-exchange to the test solution in strength. Such construction must be used in large amount of the test solutions and it is liable to enter the air bubbles in the aperture 10 at measuring so that normal measurement can not be performed.

SUMMARY OF THE INVENTION

An object of the present invention is to eliminate the above described drawbacks.

Another object of the present invention is to provide an ion selective electrode of liquid-membrane type for performing stable operation over a long period of time without depending on temperature change and moisture change.

According to the present invention there is provided an ion selective electrode comprising an outer tubular body having an opening at its one end, an inner tubular body secured to the other end of the outer tubular body and having an opening at its one end, a tip member threadingly engaged to one end of the outer tubular body and having an aperture at its one end, a first porous membrane provided between the tip member and one end of the outer tubular body to define a first reservoir together with the outer tubular body, a sealing member provided around the periphery of the first porous membrane, a second porous membrane provided at one end of the inner tubular body to define a second reservoir therein, an ion-exchanger liquid accommodated in the first reservoir and in contact with the first porous membrane directly, an internal reference solution accommodated in the second reservoir, and an inner reference electrode connected to a shielded cable extended through the other end of the outer tubular body and dipped in the internal reference solution.

The tip member for holding the first porous membrane is formed by a metal tube and at least a portion of the metal tube in contact with a solution to be tested is coated with an insulating film.

The sealing member is a paste provided between the tip member and the first porous membrane and an O-ring is provided between the porous membrane and one end of the outer tubular body.

The paste is a silicone rubber.

The O-ring is formed by a silicone rubber or a fluorocarbon resin.

DETAILED DESCRIPTION OF THE INVENTION

Figure 2:
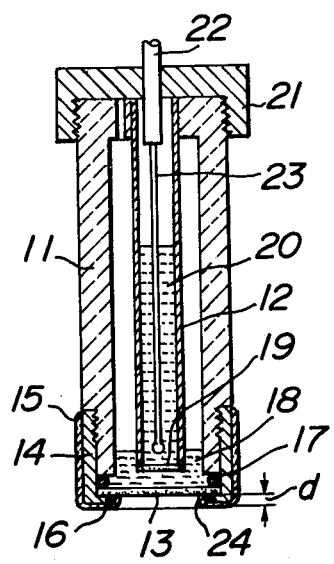
FIG. 2 is a vertical sectional view showing a construction of an ion selective electrode, in a preferred embodiment, according to the present invention.

Referring now to FIG. 2 there is shown an ion selective electrode according to the present invention. The electrode shown in this embodiment comprises an outer tubular body 11 of an insulating material, and an inner tubular body 12 supported to the outer tubular body 11 at its one end portion. The other end portion of the outer tubular body 11 is threadingly engaged with a tip member 14 which holds a porous membrane 13. The tip member 14 is formed by metallic material and coated with an insulating film 15 at its outer surface which is in contact with the test solution. As the metallic material there is any one of metals used as the material of mechanism parts but it is preferable to use the stainless steel as the metallic material in chemical characteristics and in material dynamics. The insulating film 15 is formed by spraying and drying a diluted solution of silicone resin in toluene. A portion of the tip 14 adjacent to the porous membrane 13 is coated with a paste 16 such as silicone rubber to make an outer reservoir of the ion-exchanger liquid 18 completely air-tight and an O-ring 17 of silicone rubber, Teflon (trade name) or the like is provided between the outer tubular body 11 and the porous membrane 13 in order to prevent the ion-exchanger liquid 18 contained in the outer tubular body 11 from contacting to the tip 13 directly. A porous ceramic 19 is provided at the end portion of the inner tubular body 12 opposite to the porous membrane 13 and an internal reference solution 20 is contained in the inner tubular body 12. The internal reference solution 20 is therefore conducted to the ion-exchanger liquid through the porous ceramic 19. The end portion of the outer tubular body 11 to which the inner tubular body 12 is held is threadingly engaged and sealed with a cap 21 to prevent evaporation of the ion-exchanger liquid 18 and the internal reference solution 20. A shielded cable 22 is extended through the cap 21 and entered into the reservoir of the inner tubular body 12 and an inner electrode 23 of Ag—AgCl is connected to the cable 22 so that when the cap 21 is threadingly engaged to the outer tubular body 11 the inner electrode 23 is dipped and held in the internal reference solution 20.

Accordingly to the present invention even if the ion selective electrode has the tip 14 of metallic material the outer surface thereof is coated with the insulating film 15 and the inner surface thereof is provided with the paste 16 and the O-ring 17 so that the tip 14 contact with neither the test solution nor the ion-exchanger liquid 18 and thus liberation of metallic ions contained in the metal tip 14 neither disturb the measuring of ions nor cause the mechanical reaction.

If the tip 14 by which the porous membrane 13 is held is formed by metallic material having superior mechanical strength the outer diameter of the electrode body can be made small and even if the outer diameter is made large the length d of the aperture 24 of the tip 14 can be made very small so that it is possible to effectively prevent entrance of the air bubbles and to perform measuring of the ions with a small amount of the test solutions. There is also no swell by the moisture absorption as in the plastic material so that the adhesion to the porous membrane 13 can effectively be maintained over a long period of time.

Figure 3:
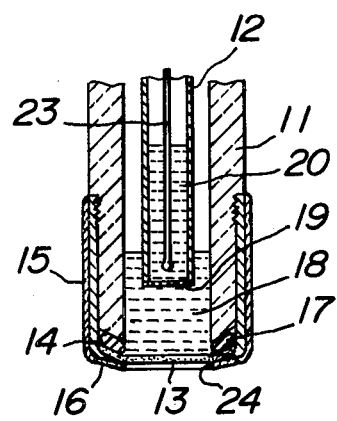
FIG. 3 is a fragmentary sectional view similar to FIG. 2 illustrating the construction of the ion selective electrode showing another modification.

FIG. 3 shows a modified embodiment of the ion selective electrode according to the present invention by partially sectional view. In this embodiment the tip member 14 has a tapered end portion by which a dish-shaped porous membrane 13 having a periphery formed in accordance with the form of the tapered end portion is held. This point is different from the electrode shown in FIG. 2. That is, the tip 14 formed by metallic material has large mechanical strength so that the end portion of the tip 14 can be made thin and thus the level of the aperture 24 of the tip 14 may substantially be coincided with that of the porous membrane 13 which is in contact with the test solution. According to this embodiment the length d of the aperture 24 shown in FIG. 2 may be made very small so that the entrance of the air bubbles can more advantageously be prevented and thus the ion measurement can be performed for very small amount of the test solution.

According to the above described invention the insulating film is coated on the portion of the metal tip in contact with the test solution and the porous membrane is held on the end portion of the tip so that the stable ion measurement can be performed over a long period of time without depending on the temperature change and the moisture change.

With the formation of the tip member by metallic material the length of the aperture of the tip which effects the test solution to the porous membrane can be made very small so that the entrance of the air bubbles may effectively be prevented and thus ion measurement can advantageously be performed for small amount of the test solution.

Figure 1:
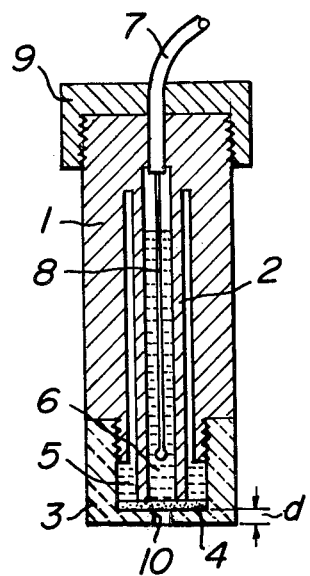
FIG. 1 is a cross-sectional view showing a construction of a conventional ion selective electrode of liquid-membrane type.

It is further understood by those skilled in the art that the foregoing description is a preferred embodiment of the disclosed electrode and that various changes and modifications may be made in the invention without departing from the spirit and scope thereof. For example, in FIGS. 2 and 3 one end of the inner tubular body 12 is contacted to the porous membrane 13 instead of utilization of the porous ceramic 19, to separately maintain the ion-exchanger liquid 18 and the internal reference solution 20 by the porous membrane 13 as in FIG. 1.

What is claimed is:

1. An improved ion selective electrode having an outer tubular body having an opening at one end, an inner tubular body secured to the other end of the outer tubular body and having an opening at one end, a tip member threadably engaged to one end of the outer tubular body and having an aperture at one end, a first porous membrane provided between the tip member and one end of the outer tubular body, to define a first reservoir together with the outer tubular body, an ion-exchanger liquid accommodated in the first reservoir and in direct contact with the first porous membrane, an internal reference solution accommodated in the second reservoir, and an inner reference electrode connected to a shielded cable, said shielded cable extending through the other end of the outer tubular body and being dipped in the internal reference solution, the improvement comprising: forming the tip member for holding the first porous membrane of a metal tube and at least a portion of the metal tube in contact with a solution to be tested being coated with an insulating film.

2. An ion selective electrode as claimed in claim 1, wherein: a sealing member is provided around the periphery of the first porous membrane.

3. An ion selective electrode as claimed in claim 2, wherein: the sealing member is formed of a paste provided between the tip member and the first porous membrane and an O-ring provided between the first porous membrane and one end of the outer tubular body.

4. An ion selective electrode as claimed in claim 3, wherein the paste is a silicone rubber.

5. An ion selective electrode as claimed in claim 3, wherein the O-ring is formed by a silicone rubber or a fluorocarbon resin.

* * * * *